United States Patent [19]

Hohlfeld et al.

[11] Patent Number: 5,022,899
[45] Date of Patent: Jun. 11, 1991

[54] SONIC DEBUBBLER FOR LIQUIDS

[75] Inventors: Robert G. Hohlfeld, 654 High St., N. Attleboro, Mass. 02760; Edward H. Thomas, Attleboro Falls, Mass.

[73] Assignee: Robert G. Hohlfeld, Attleboro, Mass.

[21] Appl. No.: 864,567

[22] Filed: May 16, 1986

Related U.S. Application Data

[63] Continuation of Ser. No. 679,707, Dec. 10, 1984, abandoned.

[51] Int. Cl.⁵ .............................................. B01D 51/08
[52] U.S. Cl. ............................................ 55/277; 55/15
[58] Field of Search ................... 55/15, 277; 210/188, 210/242.2, 695, 927

[56] References Cited

U.S. PATENT DOCUMENTS

| | | | |
|---|---|---|---|
| 2,620,894 | 12/1952 | Peterson et al. | 55/15 |
| 2,916,266 | 12/1959 | Pray | 55/277 |
| 3,103,424 | 9/1963 | Hosking | 55/277 |
| 3,239,998 | 3/1966 | Carter et al. | 55/277 |
| 3,266,631 | 8/1966 | Snaper | 55/277 |
| 3,284,991 | 11/1966 | Ploeger et al. | 55/15 |
| 3,429,743 | 2/1969 | Branson | 55/15 |
| 3,904,392 | 9/1975 | Van Inger et al. | 55/15 |
| 4,205,966 | 6/1980 | Horikawa | 55/15 |

Primary Examiner—Charles Hart
Attorney, Agent, or Firm—Cesari and McKenna

[57] ABSTRACT

A fluid debubbler 10 for removing bubbles from fluids such as blood. The debubbler utilizes an ultrasonic transducer 22 to produce low power anisotropic sound waves at about the resonant frequencies of the bubbles to be removed. The sound waves impart a force on bubbles in a fluid chamber 20 so that they will be driven towards a rejected fluid drain 18. Debubbled fluid is removed from the debubbler through an outlet port 16.

8 Claims, 3 Drawing Sheets

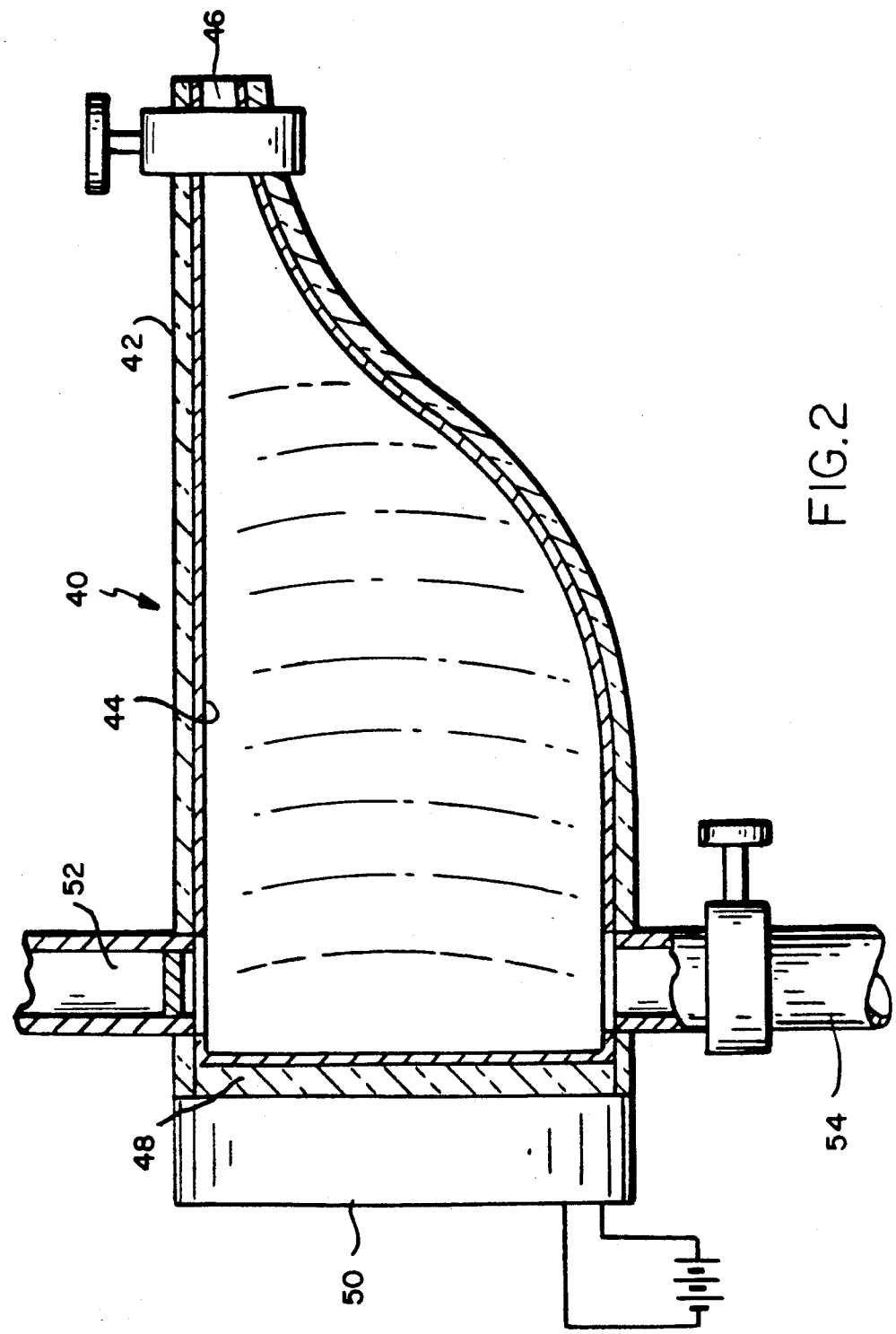

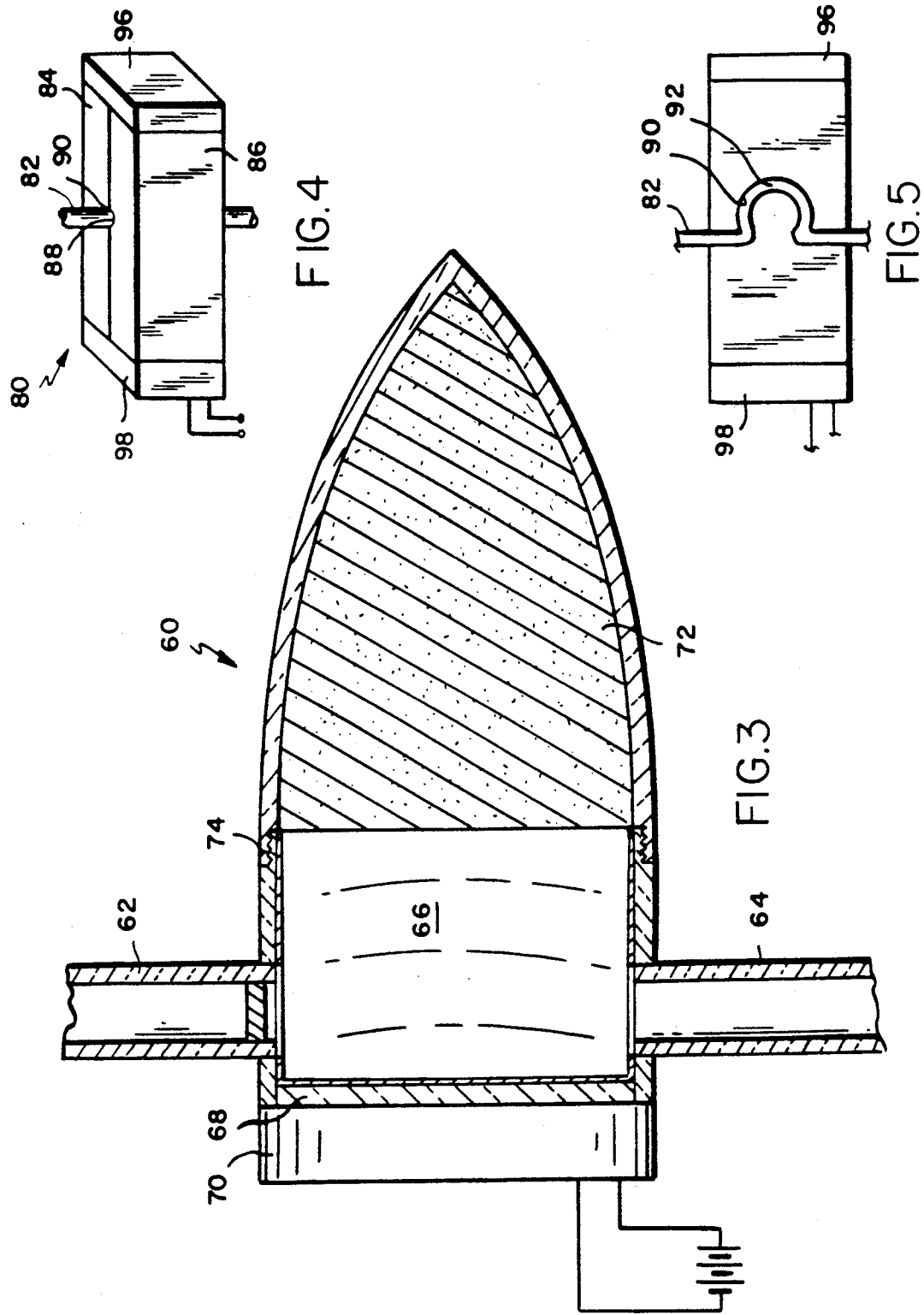

SONIC DEBUBBLER FOR LIQUIDS

This application is a continuation of application Ser. No. 679,707, filed Dec. 10, 1984, and now abandoned.

FIELD OF THE INVENTION

This invention relates to sonic debubblers of liquids and comprises a sonic debubbler which acoustically directs bubbles contained in a liquid towards a selected area.

BACKGROUND

Some liquids must be completely debubbled prior to use. For example, blood should be almost completely debubbled prior to its introduction into a patient, since it has been found that patients who are transfused for long periods of time with biological fluids are subject to confusion and disorientation. Further, in some instances, necrosis of brain and lung tissue has been found to occur. It is believed that these problems arise due to blockage of small blood vessels by microscopic gas bubbles introduced with the fluid supply.

Filters of polymeric material have long been used to remove bubbles from biological fluids, including blood supplies; such filters, however, are often inefficient. Further, these filters are incapable of reliably eliminating gas bubbles below a certain size.

Various devices have been developed that degassify liquids through the use of sound waves. Most of these devices isotropically agitate gas bubbles in a manner which makes them combine and buoyantly rise to a vapor-liquid interface, or surface. These types of device therefore, favor bubble growth and speeds up the normal outgassing of liquids streams. An example of such a device can be found in U.S. Pat. No. 3,904,392 to Van Ingen et al, in which a resonant ultrasonic horn is used to agitate bubbles which then rise to a depressurized vapor-liquid interface.

An alternate approach is to use sound waves to break up existing bubbles in a liquid and cause them to dissolve. Such devices thereby change the gas solubility of the liquid to remove the bubbles. A device using this approach is described in U.S. Pat. No. 4,205,966 to Horikawa.

Existing sonic devices, as described above, constitute an advance in the art but suffer a critical disadvantage, among others, that is particularly significant in relation to biological fluids such as blood. All these devices harmfully affect blood chemistry. The violent agitation of a liquid, as called for by some of these devices, would, in blood, result in the destruction of living blood cells, or hemolysis, due to fluid cavitation and cell rupture. Further, modification of the gas solubility of blood, as performed in others of these devices, can also have harmful effects on the blood cells. Additionally, it may permit later reformation of damaging gas bubbles.

It is an object of this invention, therefore, to provide a sonic debubbling device capable of physically removing bubbles from a liquid, particularly a biological liquid, in a non-destructive manner which leaves the liquid's gas solubility substantially unchanged.

SUMMARY OF THE INVENTION

The invention is a sonic debubbler that uses anisotropic sound waves to drive bubbles in a preferred direction and thereby divide a liquid into first and second components. The first liquid component is the debubbled component; that is, it is the component from which the sound waves have driven bubbles. The second liquid component, which forms the rejected fluid, contains the bubbles that have been driven from the first component.

After gas bubbles are physically removed from the majority of the liquid, the debubbled fluid is drawn out through a fluid outlet port. The rejected fluid can either be trapped in a disposable open cell bubble trap positioned within the container, or removed through a fluid rejection port.

The sonic debubbler of the present invention utilizes an ultrasonic pressure wave transducer (preferably, a piezoelectric transducer) to acoustically divide the liquid into the desired components. The transducer produces anisotropic sound waves that are sufficiently low in intensity to leave unperturbed the dissolved gas chemistry of the liquid but which are sufficiently strong and directional to physically impart a force to the bubbles and cause their directed movement.

In a preferred embodiment of the invention, the sonic debubbler's structure comprises a fluid container having inlet and outlet ports. An ultrasonic pressure wave transducer is placed within the container and is separated from the liquid by a film barrier. The container is preferably configured to avoid disruption of anisotropic sonic wave fronts by minimizing reflection of sonic waves. In a preferred embodiment, therefore, the container is constructed with acoustically non-reflective inner surfaces.

BRIEF DESCRIPTION OF THE DRAWINGS

The foregoing and other features and advantages of the invention will be apparent from the following, more particular description of the preferred embodiment of the invention, as illustrated in the accompanying drawings, in which like reference characters refer to the same parts throughout the different views. The drawings are not necessarily to scale, emphasis instead being placed upon illustrating the principles of the invention.

FIG. 2 is a sectional view of a second embodiment of a sonic debubbler in accordance with the invention; and FIG. 3 is an embodiment of a sonic debubbler incorporating an open cell bubble trap;

FIG. 4 is a perspective view of a sonic debubbler for an intravenous tube; and

FIG. 5 is a plan view of a component of the sonic debubbler of FIG. 4.

DETAILED DESCRIPTION OF THE INVENTION

Figure 1:
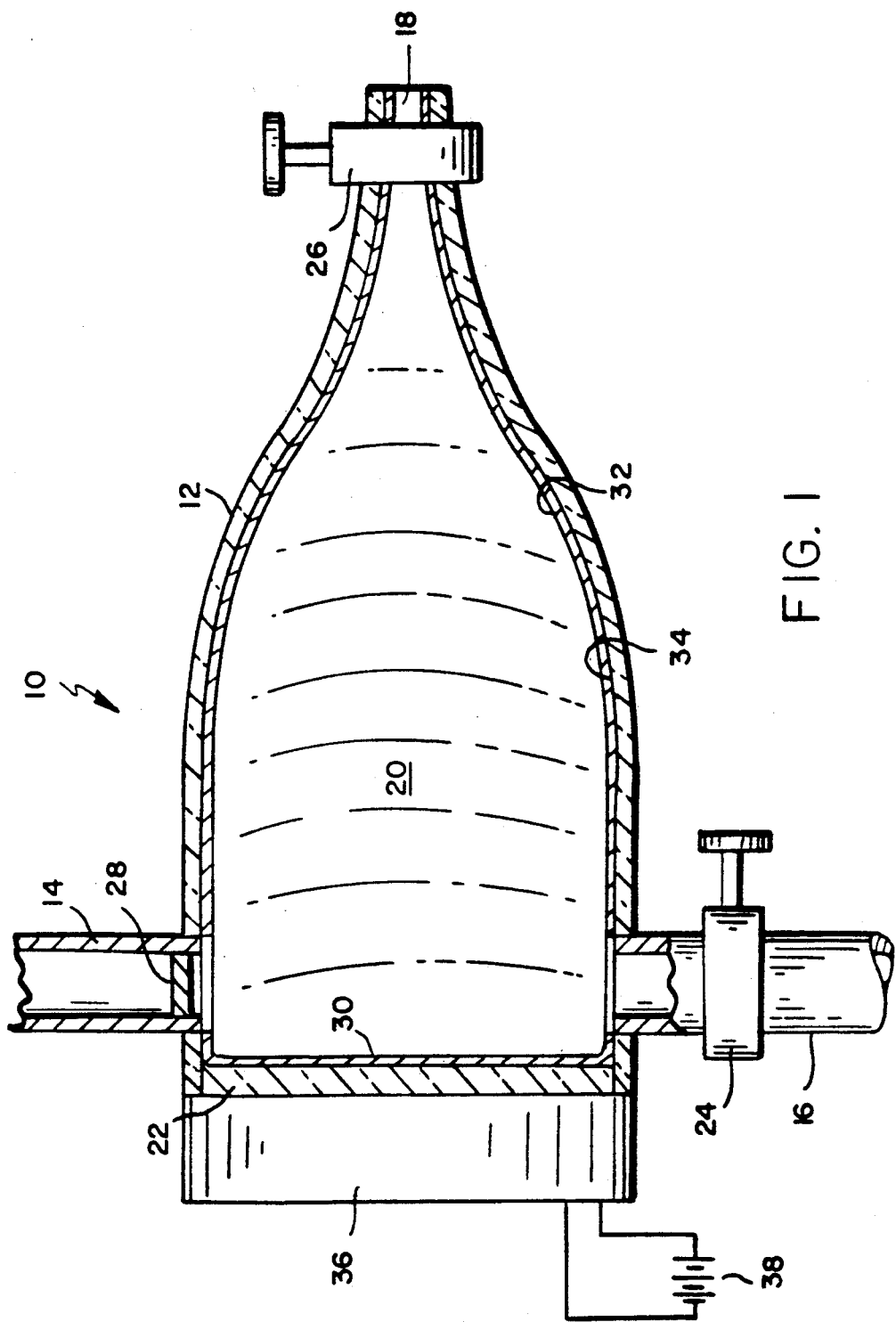
FIG. 1 is a sectional view showing a sonic debubbler embodying the principles of the invention.

In FIG. 1, a sonic debubbler 10 embodying the principles of the invention is formed from a fluid container 12 having fluid inlet and outlet ports (14, 16) and a drain port 18. The interior of the container forms a chamber 20 which contains the fluid being debubbled. The fluid container may take any of a number of forms but must be configured to permit the production of anisotropic (directed) sound waves with a minimum of reflection. A transducer 22 is located at one end of the fluid container 12. The transducer, which can be a piezoelectric, magnetostrictive, or other form of transducer, produces ultrasonic waves that apply an acoustic radiation pressure to microscopic bubbles in the liquid. This acoustic radiation pressure pushes the bubbles towards a fluid rejection or drain port 18. The movement of microscopic bubbles away from a large proportion of the fluid permits debubbled fluid to be removed from the container 12 at fluid outlet port 16.

The fluid drain port 18 must be carefully positioned so that bubbles moved by acoustic radiation are directed towards it. In this embodiment the fluid drain port is therefore placed on a tapered end of the cylinder which directs the bubbles to the port. Both the inlet and outlet ports, however, are placed adjacent to the transducer 22 in the area from which bubbles are removed. Both the outlet port 16 and the rejected fluid drain 18 are equipped with valves 24, 26, which permit adjustment and balancing of the fluid flow ratio between the ports. By varying this ratio, one can adjust the flow so that only substantially bubble free fluid passes through output port 16 and only a small portion of the fluid is drained from the fluid rejection port 18. The inlet and outlet ports 14, 16 are preferably equipped with standard intravenous (I.V.) connections (not shown) so that the inlet port can be connected directly to an I.V. bottle and the outlet port to a patient I.V. connection.

In order to produce efficient movement of bubbles, the inlet port 14 is constructed to prevent the entrance of bubbles larger than 200 microns which might not be effectively moved by the sound waves. In particular, a bubble filter 28 of polymeric material is positioned in the inlet port 14; a typical mesh size for such a filter is between 20 and 170 microns. Bubbles smaller than the filter mesh size pass through the filter and are transported to the fluid rejection port by the sound waves.

The transducer 22 is protected from contact with the liquid by a thin film 30 of flexible material interspaced between the fluid in the chamber 20 and the transducer 22. This thin film 30 permits passage of the ultrasonic waves while preventing fluids from damaging the transducer. While various plastic films are useful for forming this barrier, both the plastic film and the inside of the container must be biologically inert so as to avoid contamination of the fluid in the chamber 20.

Sound wave reflection must be minimized to prevent disruption of the sonic wave fronts otherwise the bubbles would only vibrate about a neutral position and not be transported. This can be done in at least two ways; one is by specially shaping the fluid container to avoid reflective surfaces that might change the path of the sound waves, while the other is to use impedancematched acoustic layers 32 on the inside of the fluid chamber 20 to eliminate sound wave reflection from surfaces.

In this embodiment (FIG. 1), we have utilized impedance matched acoustic layers 32 made of tungsten doped epoxy to eliminate sound wave reflection. However, many other high acoustic impedance materials could be used. The layer is approximately a quarter wavelength thick at the frequency of the sound wave generated by the transducer. As a result, sound impinging on the layer, and reflecting back from the inner wall 34 will be one-half of a wavelength out of phase with the wave front at the surface of the layer and the resultant is a net cancellation of sound intensity at the surface. Although this diminishes sonic wave strength to some extent, it prevents disruption of the directed wave fronts. The use of impedence matched layers 32 thereby prevents the bubbles from being driven back towards the transducer 22 by reflected sound waves.

The transducer 22 produces anisotropic sound waves which travel across the fluid chamber 20 from left to right as shown in FIG. 1. The sound waves apply an acoustic radiation pressure to bubbles contained in the fluid. Since these sound waves are directional (anisotropic), bubbles are driven towards the drain 18. The acoustic radiation pressure that acts on the bubbles is known in classical acoustics as Rayleigh sound radiation pressure. A useful discussion of this radiation pressure is found in the reference *Physical and Applied Acoustics: an Introduction,* Meyer, E., and Newman, E.G., Academic Press, N.Y. (1972), pgs. 116-124.

In accordance with the present invention, bubbles in the fluid cavity are given a net force that drives them towards the drain 18 by operating the transducer at frequencies corresponding to the resonant frequencies of the bubbles. This results in the needed momentum transfer for effective removal of bubbles while maintaining the power input to the fluid at a level below that which may adversely affect the fluid chemistry. For example, when the fluid is human blood, it is essential that the power levels remain below that which would cause hemolysis which can result from cavitation in the fluid. It should also be noted that blood cells and proteins are not transported since they absorb very little acoustic radiation. This is because they are mostly liquid and are therefore substantially impedance matched to the surrounding fluid.

In order to effectively move a variety of bubbles in a range of sizes (5 to 200 microns), the sound wave generated by the transducer must combine a sufficient number of wavelengths to encompass the resonant frequencies of a range of bubble sizes, while still being of sufficiently low power to leave undisturbed the dissolved gas chemistry. As mentioned above, this is particularly important when debubbled biological liquids such as blood which can be rendered useless or even harmful by changes in their chemistry. In order to accomplish this goal the transducer 22 is tuned to provide a broad band ultrasonic signal. Alternatively, the signal frequency, and thus wavelength, can be varied in time over the desired wavelength range to effect a variety of bubble sizes. Either solution can be accomplished through the use of drive circuitry 36 which is connected to an external power supply 38. The external power supply may take the form of a transformer for connection to a standard electrical outlet or a battery pack.

In the present invention, for example, bubble sizes of from 5 to 100 microns are effectively removed by operating the transducer at wavelengths of from 0.28 to 4.7 centimeters with frequencies of from 540 kHZ to 32 kHZ and at a low power level of less than approximately 100 mw/cm$^2$. This is significantly below that required to remove gas in systems which operate by varying the fluid equilibrium relationship and is also well below the threshold at which damage may be caused to the fluid and its constituents. Indeed, the low power level required is significantly below the U.S. Government's maximum power level permitted for ultrasonic scanning of hospital patients.

The utilization of a unidirectional Rayleigh pressure wave to sweep bubbles from a fluid volume contrasts with the methods of operation used in prior art ultrasonic degasifying devices wherein multi-directional pressure waves, aided by multiple reflections, is encouraged and stimulated in order to agitate bubbles and promote bubble growth. Multiple reflection of the acoustic waves results in the creation of an approximately isotropic sound wave field which fills the fluid container and effects no net transfer of momentum to the bubbles. This results in no net bubble movement except as a result of bubble buoyancy. In the present invention, in contrast, momentum is imparted to the bubbles by the anisotropic (directed) sound waves. The sound waves discussed herein produce a maximal momentum transfer to the bubbles to quickly drive them towards the fluid rejection port.

In FIG. 2 is shown a liquid debubbler 40 in which the fluid container 42 has a geometry differing slightly from that shown FIG. 1. The fluid container 42 is modified for those fluids where bubble bouyancy is an important factor. As a result, the uppermost wall 44 of the container 42 is flat and cuts in half, along its longitudal axis, the otherwise bottle-like container 42. The shape of the container, therefore, when properly oriented, prevents trapping of bubbles in cavities away from the fluid rejection port. Buoyant bubbles are driven along the wall 44 towards rejection port 46 by the sound wave produced by the transducer 48. The internal surfaces of the container including wall 44, are coated with a quarter-wave acoustic layer as discussed above.

The inlet port 52, the outlet port 54 and the drive circuitry 50 are in all respects identical to that described in relation to FIG. 1.

FIG. 3 shows yet another form of debubbler in accordance with the invention. As was previously the case, the debubbler 60 has a fluid inlet port 62, a fluid outlet port 64 and a fluid chamber 66. A transducer 68 driven from a driver 70 generates acoustic signals as previously. However, instead of a drain port for rejected fluid, there is provided an impedance matched acoustically non-reflective bubble trap 72 in the form of an open-cell sponge which receives the bubble-laden fluid directed to it by the unidirectional sound wave. Fully debubbled liquid is then removed through fluid outlet 64. Large amounts of bubbles are absorbed by the bubble trap 72 before it is filled with bubbles and needs replacement.

A flange mechanism 74 interposed on the walls of the cylinder permits easy removal and exchange of the disposable bubble trap 72. Usage requirements will dictate the frequency of changing the bubble trap 72.

It should also be noted that the free volume of the fluid chamber 66 has been significantly shortened in this embodiment as compared with the embodiments discussed in relation to FIGS. 1 and 2. As a result, non-reflective acoustic layers are not required in the fluid chamber 66, since little sonic reflection occurs in the foreshortened fluid container.

The piezo-electric transducer 68, the inlet port 62, the outlet port 64 and drive circuitry 70 are otherwise identical to those discussed in reference to the other embodiments.

FIGS. 4 and 5 show a portable blood debubbler 80 for attachment to a conventional disposable IV line 82. This device is placed on the IV line in between the IV supply and the patient during transfusions.

The portable debubbler comprises two wave guide blocks 84, 86 preferably of a clear plastic, such as Lexan. The wave guides have grooves 88, 90 which form a partial loop in the IV line as shown in the disassembled view of the wave guide (FIG. 5).

The loop in the IV line acts as a bubble trap during operation of the debubbler. Sonic waves from an ultrasonic transducer pass through the wave guide and IV tube pushing bubbles toward the right side of the debubbler (as depicted in the drawings). Bubbles would therefore have to travel against the sound pressure waves to exit to loop 92. In normal flow conditions, this is impossible and bubbles are thereby trapped in the loop and will not be transported to the patient. The bubbles in the loop do not build up substantially since the loop is reset each time an IV set is changed.

This device has an added advantage over those discussed above since sterility problems are completely avoided. The IV fluid never leaves the IV set or contacts the debubbler. The debubbler therefore cannot pass any impurities into the fluid stream and need not be sterilized.

In order to prevent sound wave reflection in this embodiment, a sound absorbent layer 96 is used to absorb the ultrasonic waves after they pass through the wave guides 84, 86.

Typically, the debubbler need only be as large as is required for complete wave formation. For example, waves to remove 100 micron bubbles require a combined wave guide about 5 centimeters wide.

Other aspects of this debubbler, and in particular the drive circuitry 98, are identical to those discussed in reference to the other embodiments.

While the invention has been particularly shown and described with reference to the preferred embodiments thereof, it will be understood by those skilled in the art that various changes in form may be made therein without departing from the spirit or scope of the invention as described in the appended claims. For example, although the invention has been largely described with reference to biological fluids such as blood, liquid debubblers embodying the principles of this invention may be quite useful for preparing chemicals for chemical synthesis reactions, particularly where gas solubility is an important factor.

We claim:

1. A fluid debubbler device for removing gas bubbles from a liquid having a specific gas solubility comprising:
   a fluid container, having an inner surface coated with an acoustically anti-reflective coating which reduces acoustic wave reflections, for containing a liquid from which bubbles are to be removed;
   a fluid inlet port positioned in a wall of said fluid container;
   a fluid outlet port positioned in a wall of said fluid container; and
   a pressure wave transducer that produces an acoustic wave in said liquid in response to an energy source, said pressure wave transducer being positioned so that the Rayleigh pressure of the acoustic wave drives said gas bubbles away from said fluid outlet port without substantially changing the gas solubility of said liquid.

2. The fluid debubbler device of claim 1 wherein said acoustically anti-reflective coating is of sufficient thickness so that about one quarter of said accoustic wave passes through said accoustically anti-reflective coating prior to its reaching an inner surface of said container.

3. The fluid debubbler device of claim 1 wherein said anti-reflective coating is biologically inert.

4. A debubbler as defined in claim 1 wherein the pressure wave transducer introduces pressure waves having a range of frequencies and thus having the resonant frequencies of bubbles of a range of sizes.

5. A fluid debubbler for removing gas bubbles from a biological fluid, the debubbler comprising:
   A. a sonic waveguide, providing a channel having a channel inlet and a channel outlet and adapted to receive therein a tube of biological fluid extending form the channel inlet to the channel outlet, for conducting sound waves introduced at one end of the waveguide along the waveguide and through the biological fluid flowing through the channel, the waveguide conducting the sound waves in a preferred direction against the direction of at least a reverse-direction segment of the path of the channel from the channel inlet to the channel outlet; and B. a transducer coupled to the one end of the waveguide for introduction of sound waves thereinto, whereby the Rayleigh pressure on any bubbles entrained in biological fluid flowing in the tube from the channel inlet to the channel outlet tends to prevent those bubbles from traveling with the biological fluid in the reverse-direction segment toward the channel outlet.

6. The fluid debubbler device of claim 5 further comprising a sound absorbent layer to prevent sonic reflection in said wave guide.

7. The fluid debubbler device of claim 5 wherein said debubbler is portable.

8. A debubbler as defined in claim 5 wherein the transducer introduces pressure waves having a range of frequencies and thus having the resonant frequencies of bubbles of a range of sizes.

* * * * *